(12) United States Patent
Newcomb

(10) Patent No.: US 10,912,851 B2
(45) Date of Patent: Feb. 9, 2021

(54) MODULAR APPARATUS FOR RECEIVING, STOWING, STERILIZATION, DELIVERY, AND PICKUP OF A PACKAGE

(71) Applicant: Royce Newcomb, Fresno, CA (US)

(72) Inventor: Royce Newcomb, Fresno, CA (US)

( * ) Notice: Subject to any disclaimer, the term of this patent is extended or adjusted under 35 U.S.C. 154(b) by 0 days.

(21) Appl. No.: 16/918,614

(22) Filed: Jul. 1, 2020

(65) Prior Publication Data
US 2020/0330631 A1    Oct. 22, 2020

Related U.S. Application Data

(60) Provisional application No. 63/001,459, filed on Mar. 29, 2020, provisional application No. 63/001,440, filed on Mar. 29, 2020.

(51) Int. Cl.
| | | |
|---|---|---|
| *A61L 2/10* | (2006.01) | |
| *A61L 2/24* | (2006.01) | |
| *G06K 7/10* | (2006.01) | |
| *H04W 84/04* | (2009.01) | |
| *H04W 84/12* | (2009.01) | |

(52) U.S. Cl.
CPC .................. *A61L 2/10* (2013.01); *A61L 2/24* (2013.01); *G06K 7/10366* (2013.01); *A61L 2202/11* (2013.01); *A61L 2202/121* (2013.01); *A61L 2202/122* (2013.01); *A61L 2202/14* (2013.01); *A61L 2202/23* (2013.01); *H04W 84/042* (2013.01); *H04W 84/12* (2013.01)

(58) Field of Classification Search
CPC ........ A61L 2/00; A61L 2/0029; A61L 2/0047; A61L 2/02; A61L 2/08; A61L 2/10
USPC ................. 250/492.1, 493.1, 453.11, 455.11
See application file for complete search history.

(56) References Cited

U.S. PATENT DOCUMENTS

| | | | |
|---|---|---|---|
| 2005/0023483 A1* | 2/2005 | Fenc ........................ | A61L 2/10 250/455.11 |
| 2008/0021307 A1* | 1/2008 | Freeman ................. | A61L 2/081 600/424 |
| 2015/0118107 A1* | 4/2015 | Sunkara ................. | A61B 90/98 422/24 |
| 2017/0100496 A1* | 4/2017 | Shur ....................... | A23L 3/003 |
| 2018/0185529 A1* | 7/2018 | Shur ....................... | G01V 8/20 |
| 2018/0193500 A1* | 7/2018 | Safavi ................... | B08B 7/0057 |
| 2020/0078480 A1* | 3/2020 | Starkweather ........... | A61L 2/10 |

* cited by examiner

*Primary Examiner* — Jason L McCormack
(74) *Attorney, Agent, or Firm* — Sherman IP LLP; Kenneth L. Sherman; Steven Laut

(57) ABSTRACT

The present invention is directed to an apparatus for receiving, stowing, sterilizing, delivery, and pick-up of a package. In one case, the package can be an unattended package which cannot be received by the consumer. In another case, the package can be a package that has to be disinfected first to be received by the consumer. The apparatus comprises a frame and an enclosure mounted in the frame. The enclosure including one or more storage compartments for receiving and stowing the package. The apparatus further comprises a digital locking feature to control access to the enclosure and UV-lamps for disinfection of the package.

17 Claims, 9 Drawing Sheets

MODULAR APPARATUS FOR RECEIVING, STOWING, STERILIZATION, DELIVERY, AND PICKUP OF A PACKAGE

CROSS-REFERENCE TO RELATED APPLICATIONS

This application claims priority to the U.S. provisional patent application Ser. No. 63/001,459, and the U.S. provisional patent application Ser. No. 63/001,440 filed on Mar. 29, 2020, which are incorporated herein by reference in their entirety.

FIELD OF INVENTION

The present invention relates to an apparatus for receiving and stowing of items, and in more particularly relates to an apparatus and method for receiving, stowing, sanitization, delivery, and pickup of a courier package, the apparatus can be customized for both residential and commercial places.

BACKGROUND

An e-commerce online shopping has grown exponentially in the last decade. A consumer can now order a range of items including household items, office supplies, mechanical tools, and like through a website, mobile application, or over a call. The logistics supply the ordered items directly to the consumer's address. Local vendors or stores also prefer to deliver items from their central warehouses to the consumers directly, rather than stocking the items at the stores. Also, consumers receive daily food product supplies including milk and groceries. There has been an increasing trend of ordering items to be delivered to the consumer's address rather than the consumer visiting the local vendors to purchase the products.

Also, certain situations, such as the spread of an epidemic disease may limit the movement of people. Also, such epidemic conditions may confine people to their houses. It is preferred in such situation that essential supplies are delivered directly to the consumers address, rather the consumers visiting the stores.

However, delivering the items directly to the consumer's address or picking up returns directly from the consumers can be problematic for several reasons. For example, the consumer may not be available at the address to receive the ordered items. Also, in an epidemic situation, it may not be preferred that the consumer is directly exposed to the deliveries or comes in close contact with the delivery person for delivery or pick-up. However, in both the situation, the delivery person generally leaves the deliveries unattended at the door or other suitable place. Redelivering the items can be both costly and time-consuming. Such unattended deliveries may be subject to theft or damage due to external elements. The external factors include weather, and in particular, the perishable items and pharmaceuticals are particularly susceptible to damage by elevated temperatures or direct exposure to the sunlight. Also, the deliveries may not get picked up for a long duration of time. For example, while the consumer is traveling, he may not be able to pick the deliveries soon. The deliveries left outside for an extended period have a greater risk of theft and damage. Thus, a need is appreciated for an apparatus that can safely receive the deliveries and secure them until taken up by the consumer. Moreover, a need is appreciated for the apparatus that can secure returns until picked by the delivery person.

For any variety of reasons, leaving deliveries exposed to the damaging elements, theft, draw attention to, or cause concern or stress to either the delivering or receiving party is not necessary and is avoidable with the present invention.

The term "package" is used herein to describe any type of package, parcel, bag, or items. The items may be loose or packed. The items include ordered items being delivered to the consumer's address. The items include food items, groceries, household items, office supplies, pharmaceuticals, newspaper, and like items that can be delivered to the consumer's address.

The term "consumer" is used to describe any person who has ordered the items to be delivered to the consumer's address and includes agents or relatives of the consumer.

The terms "consumer's address" or "address" are used interchangeably hereinafter and used to describe a place including a residential place such as home and a business place such as an office.

The term "deliveries" is used herein to describe a package to be delivered or is delivered to the consumer's address.

SUMMARY OF THE INVENTION

The principal object of the present invention is therefore directed to an apparatus for safely receiving and securing the deliveries.

It is an additional object of the present invention that the apparatus can protect unattended deliveries from theft.

It is still an additional object of the present invention that the apparatus can save the deliveries from damage due to external factors.

It is yet an additional object of the present invention that the apparatus provides for the UV-C sterilization of deliveries.

It is a further object of the present invention that the apparatus secures the deliveries under prescribed temperature conditions.

It is still a further object of the present invention that the apparatus could be remotely operated.

It is yet a further object of the present invention that the apparatus provides timely notifications to the consumer.

It is another object of the present invention that the apparatus can have position coordinates for navigation to the apparatus.

It is still another object of the present invention that the apparatus can record activity near the apparatus for safety.

It is yet another object of the present invention that the apparatus is easy to install and use.

It is a further object of the present invention that the apparatus allows for contactless delivery a package.

It is still a further object of the present invention that the apparatus allows for contactless pickup of the returns.

It is also an object of the present invention that the apparatus provides for maintaining social distancing in an epidemic situation.

In one aspect, the present invention is directed to an apparatus for receiving and securing a package. In one case, the package can be an unattended package which cannot be received by the consumer. In another case, the package can be a package that has to be disinfected first to be received by the consumer. In one aspect, the apparatus comprises a frame and an enclosure mounted to the frame. The enclosure including one or more storage compartments for receiving and securing the package. The apparatus further comprises a locking feature to control access to the storage compartment. In one case, the locking feature is a digital lock coupled to the enclosure to control the opening of the enclosure for gaining access to the storage compartments. In one case, the locking feature can be digitally operated.

In one aspect, the apparatus further comprises a control unit in communication with the locking feature. The control unit comprises a network circuitry that allows the control unit to connect to a network for sending and receiving instructions or data packets between the control unit and a remote user device. In one case, the remote user device could be a smartphone or remote control. In one case, the network can be wired or wireless. In one case, the control unit can operate to lock and unlock the apparatus.

In one aspect, the apparatus further comprises a refrigeration unit coupled to the frame for regulating the temperature inside the enclosure within predefined limits. In one case, the consumer can set the predefined limits. In one case, the delivery person can set the predefined limits. In one case, the predefined limits can be remotely set by the consumer through the user device. In one case, the apparatus can read the predefined limits from a tag coupled to the package. The tag can be an RFID tag and the apparatus can comprise an RFID reader.

In one aspect, the apparatus comprises one or more UV lamps configured to provide ultraviolet rays in a UV-C region. The UV lamps positioned such as to irradiate the storage compartments, and in more particular to irradiate the package contained in the storage compartments. The UV lamps can be coupled to the control unit, wherein the control unit has a timer circuitry. The control unit operates the UV lamps for a predetermined duration, wherein the predetermine duration can be configured by the timer circuitry. The predetermined duration can be pre-set by the consumer. In another case, the predetermined duration can be remotely set by the consumer using the user device.

In one aspect, the apparatus further comprises a night vision 2-way camera & audio security system for recording activity near the apparatus. The camera can record any activity near the apparatus for security reasons. For example, the camera can record any suspicious activity nearby the apparatus. The camera can further record the persons accessing the apparatus. In one case, the apparatus can also record a package being kept inside the enclosure of the apparatus.

In one aspect, the apparatus comprises a frame mountable on a floor or a wall. The frame having several enclosures, each enclosure having a door providing access to the enclosure. Each enclosure has a rear wall opposite to the door, left wall, right wall, a top wall, and a bottom wall. Each enclosure can have one or more storage compartments. The door is pivotally coupled at one end to the frame, while one of the other ends is provided with the locking feature to secure the door to the frame. The top of the frame can be provided with the camera. In one case, multiple wall divide an inner space of a large enclosure into several enclosers each having a separate door. Such an embodiment of the present invention can hereinafter refer to as eBox retro curbside. Such as apparatus is more suitable for curbside, such as a near market corner, retail establishments and like. The eBox retro curbside can be subscribed by several customers, wherein each of the enclosure of the eBox retro curbside can have a unique customer address.

In one aspect, the present invention provides a compact form of the apparatus which has only one enclosure and is more suitable for residential places, single offices, and rooms. The apparatus includes a frame that can mount to a wall. The enclosure having the front side, a rear side, a left side, a right side, a bottom side, and a top cover. The front side of the enclosure is having a handle that can be grabbed by hand to unfold the enclosure from its nested configuration.

The apparatus in unused condition can be folded into a nested configuring, wherein the front side of the enclosure collapses towards its rear side, thus saving space. The left side and the right side of the apparatus, each is made of two panels joined by a hinge joint, such as the left side and the right side can collapse inwards when the front side is pushed towards the rear side. The apparatus further includes a first chamber and a second chamber each adjacent to the rear side of the enclosure. The width and area of the first chamber and the second chamber can be commensurate with the width and area of the top cover and the bottom side, respectively. The bottom side is rigid enough to withstand the weight of a package stored upon the bottom side and flexible enough to be retracted into the second chamber. The top cover can be retracted into the first chamber. The retracting of the top cover, the bottom side and collapsing of the left side and the right side allows the enclosure to be collapsed into a nested configuration. Similarly, the bottom side and the top cover can be extended from the first chamber and the second chamber for securing the package. Once, the package is placed in the enclosure, the top cover can be locked. To retrieve the package, the top cover can be unlocked and top over can be retracted back into the first chamber. Upon pick-up of the package, the bottom side can be retracted back into the second chamber, and the front side can be pushed towards the rear side for collapsing the enclosure in the nested configuration. Such as apparatus can be hereinafter referred to as eBox retro advantage.

These and other objects and advantages of the embodiments herein will become readily apparent from the following detailed description.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
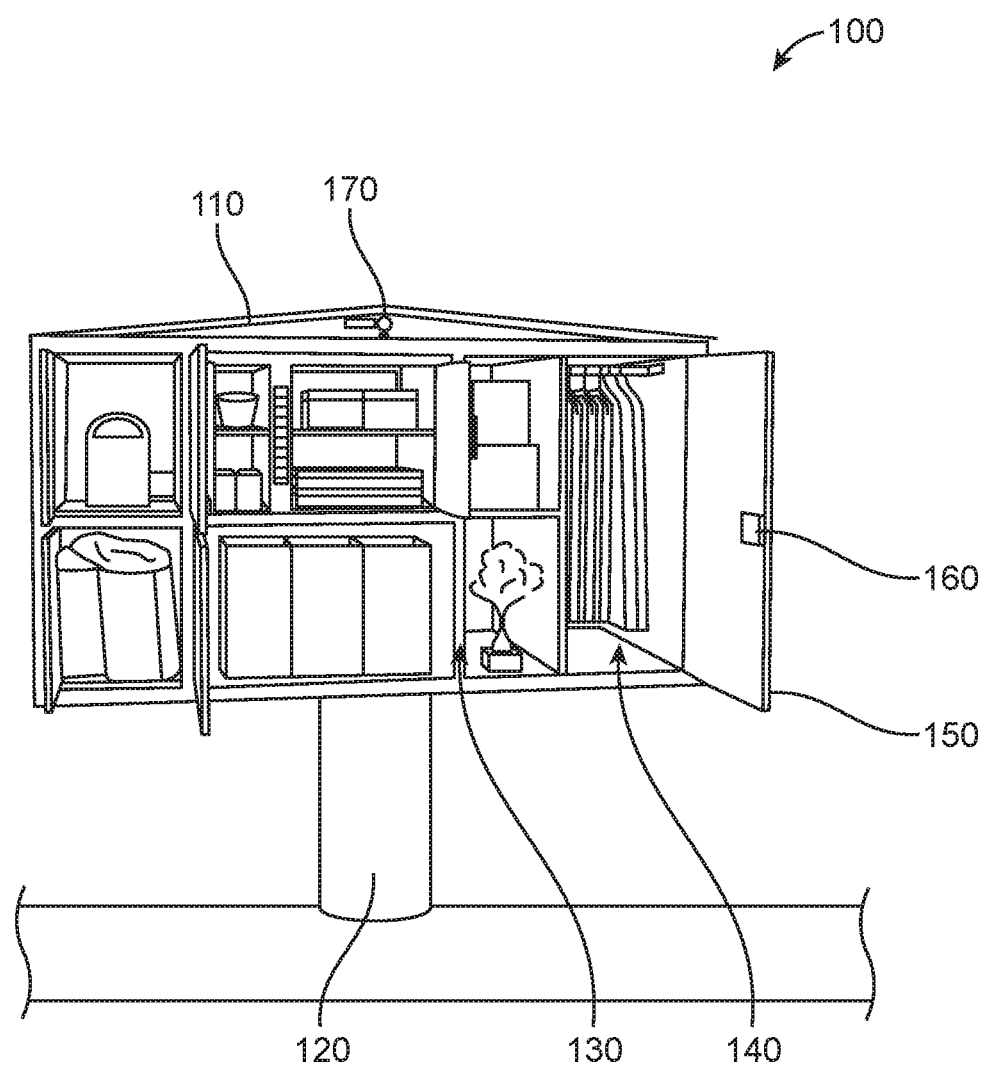
FIG. 1 is a perspective view of eBox retro curbside, according to an embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, the drawings may not be to scale.

Now referring to FIG. 1 which shows an embodiment of the eBox retro curbside apparatus for receiving and securing a package. The apparatus 100 includes a frame 110 mounted to a stand 120, wherein the stand 120 can be mounted to the ground. The frame 110 can be a large enclosure having a rear side, left, right, top, and bottom sides, the front is open. Multiple walls 130 divide the main enclosure of the frame into multiple enclosures 140. To each of the enclosure 140 is provided a door 150 for closing the enclosure. Also, the door 150 can be provided with a digital lock 160 which can secure the door 150 to the frame 110 or walls of the frame 130. The door 150 can be mounted to the frame 110 using a hinge joint (not shown). In one implementation, the enclosure can include one or more storage compartments. One or more storage compartments can be of the same size or varied sizes. Varied sizes of compartments can store packages of assorted sizes. In one case, the eBox retro curbside type apparatus according to the present invention can be designed for all types of secure and versatile interior and exterior installations.

Figure 2:
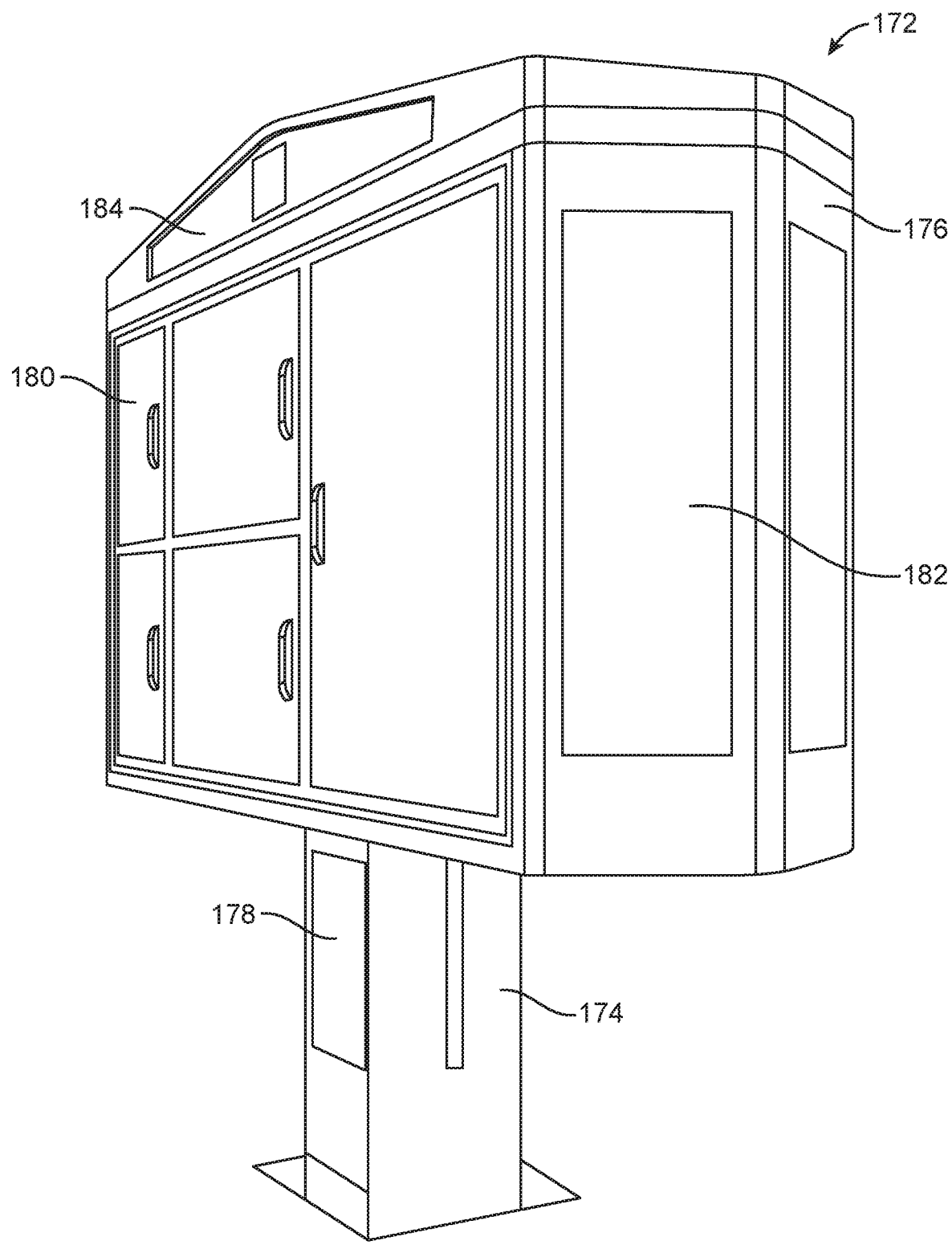
FIG. 2 is another view of the eBox retro curbside, according to an embodiment of the present invention.

FIG. 2 shows an alternate implementation of the apparatus of FIG. 1 which is also a curbside apparatus 172 having a stand 174 and a frame 176 mounted on the stand 174. The stand is having a display 178 on its front side. The frame 176 is having multiple enclosures 180. Moreover, the frame 176 is further multiple displays 182 on its side and a display 184 near top. At least one display can be used as an interface wherein a user can interact with the apparatus through the interface. One or more displays can be used for advertising products and services. Moreover, at least one display can be used to aid a user in operating the apparatus.

Figure 3:
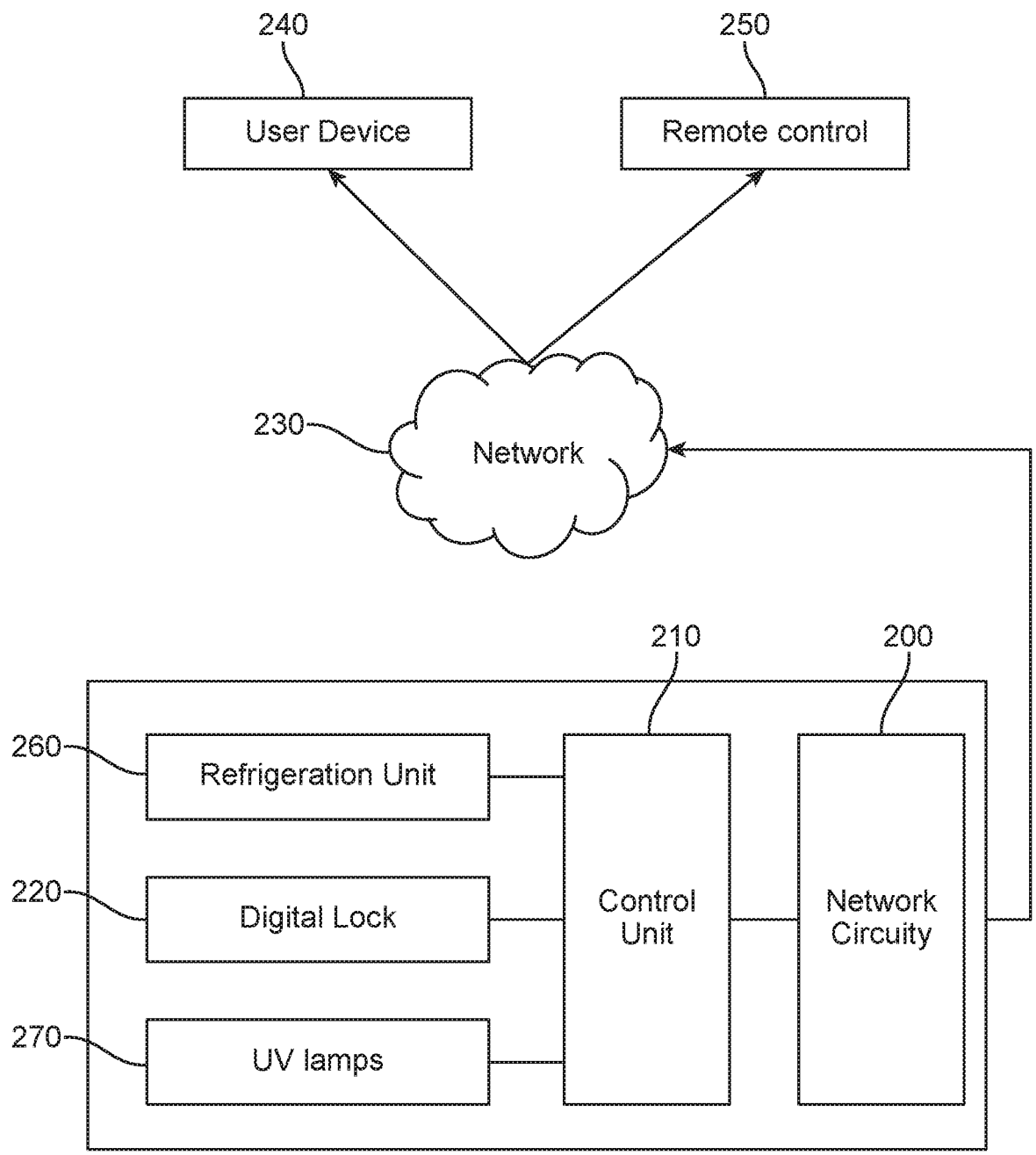
FIG. 3 is a block diagram showing components of the apparatus, according to an embodiment of the present invention.

As shown in FIG. 3, the apparatus can comprise a control unit 210 which can be coupled to one or more components of the apparatus for controlling the function of the one or more components. The control unit 210 can include a network circuitry 200 configured for wired or wireless communication to a network 230. The network can be a cellular communication network, LTE, UMTS, WiMAX, EV-DO, CDMA, GSM, Bluetooth, Bluetooth Low Energy, Bluetooth Smart, Wireless Fidelity (Wi-Fi), Zigbee, ANT, ANT+, Thread, Internet Protocol (IP), Ethernet, Fast Ethernet, Gigabit Ethernet, ATM, FDDI, Near Field Communication (NFC), or any other network known to a skilled person for sharing data packets between two electronic devices. In one case, the network can be a cloud network. In one case, the control unit 210 can be connected to a user device 240 or a remote control 250 through the network 230. The user device 240 can receive notifications from the control device and can send instructions to the control unit 210. The user device 240 can also receive images or videos from the control unit 210. In one case, the user device 240 is wirelessly connected to the control unit 210. In one case, the remote control can be wired to the control unit 210.

The digital lock 220 can be operably connected to the control unit 210 for switching the digital lock between an open position and a closed position. The control unit 210, in turn, can be instructed by the remote control 250 or the user device 240 to lock or unlock the digital lock. The digital lock can be based on electronic keys that are unique to a digital lock. These electronic keys can be generated by a secure algorithm based on the code and hardware of the digital lock. These keys can then be configured into the user device 240 for operating the digital lock. In one case, the electronic keys can be generated by SSL based algorithms.

In one embodiment, the apparatus further comprises a refrigeration unit 260 for regulating the temperature inside the enclosure within predefined limits. The refrigeration unit 260 can be coupled to the control unit for controlling the operation of the refrigeration unit 260. The refrigeration unit 260 can be used to regulate the temperature of the enclosure when any perishable items, like milk, food, vegetable, and like are stored in the apparatus. In one case, the consumer can set the predefined limits. In one case, the delivery person can set the predefined limits. In one case, the predefined limits can be remotely set by the consumer through the user device 240. In one case, the apparatus can read the predefined limits from a tag coupled to the package. The package can be provided with a tag containing storage information for the package. A suitable reader can be provided in the apparatus that can read the tag and set the temperature of the refrigeration unit 260. In one case, the tag can be an RFID tag and the apparatus can comprise an RFID reader. The RFID reader can be coupled to the refrigeration unit 260 or the control unit 210. The refrigeration unit 260 can be used as and when required. Perhaps the refrigeration unit can be used when a perishable item or any other item which needs to be stored under lower temperature conditions. For example, certain biological medicines must be stored at a lower temperature condition. Thus, the present invention keeps the packages safe, secure, and fresh in optimum temperature-controlled environment.

In one embodiment, the apparatus can include one or more UV lamps 270 configured to provide ultraviolet rays in the UV-C region. The UV lamps 270 can be positioned inside the enclosure such as to irradiate the storage compartments, and in more particular to irradiate the package contained in the storage compartments. The UV lamps 270 can be coupled to the control unit 210 for controlling the operation of the UV lamps. The number of UV lamps can vary based on the size of the enclosure. Construction and working of the UV lamps are known in the art. It is known that ultraviolet rays in the UV-C region, when irritated on an object for sufficient time, can kill microorganisms including bacteria, yeast, and viruses. Coronaviruses can also be killed by UV-C irradiation. The control unit 210 can be provided with a timing circuitry to track the time and duration of operating the UV-lamps. Now, the control unit can be configured to turn the UV lamps On, whenever a package is placed inside the apparatus and the apparatus is closed. The UV lamps can run for a predetermined duration. Alternatively, the UV lamps can be turned On by the delivery person or the consumer through the user device 240. In one case, the predetermined duration can be pre-set by the consumer into the control unit 210. In another case, the predetermined duration can be remotely set by the consumer using the user device 240. Thus, the present invention can be advantageous by automatically and safely sanitizing the packages using the UV light sanitizing feature of the present invention.

In one embodiment, the apparatus can further comprise a camera and a microphone. FIG. 1 shows a camera 170 mounted on top of frame 110. The camera can be preferably a 1080p HD wire-free night vision 2-way camera & audio security. The camera provides an additional security feature to the apparatus. In one implementation, the camera and security system can be equipped with motion detection with auto alert and auto record features. Custom geofence zone can be set by the user that allows the user to define the alert zones. The camera 170 can be coupled to the control unit 210 of the apparatus and can be controlled by the user device. The user can do live view recording in case the user notices suspicious activity. The output from the camera can be transmitted to the user device 240 through the control unit. The output of the camera can also be recorded to a device wire or wirelessly coupled to the control unit 210. For example, the control unit 210 can be coupled to a remote device through a Wi-Fi network for recording the output of the camera. The microphone can record the nearby sounds. The camera can also record the persons accessing the apparatus. In one case, the apparatus can also record the package being kept inside the enclosure of the apparatus.

In one embodiment, the present invention can embody features of the internet of things (IoT) for monitoring and managing the functioning of the apparatus including receiving and storing the package and controlling the conditions of storage of the apparatus.

Figure 4:
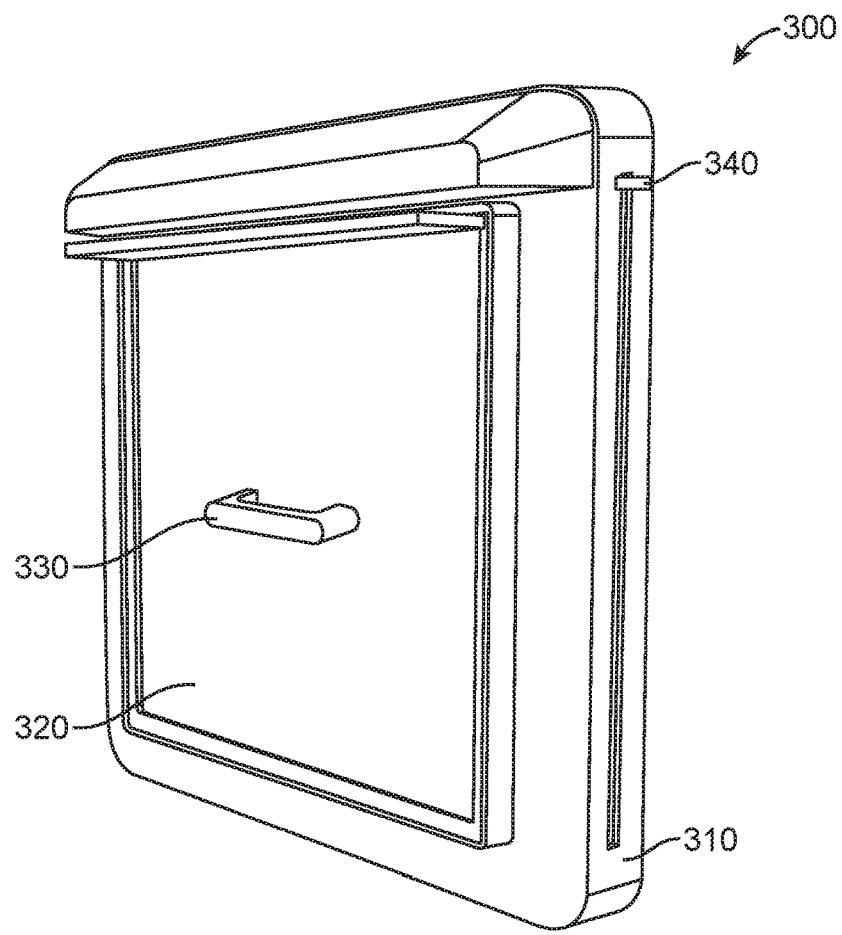
FIG. 4 is a perspective view of eBox retro advantage, according to the present invention.
Figure 5:
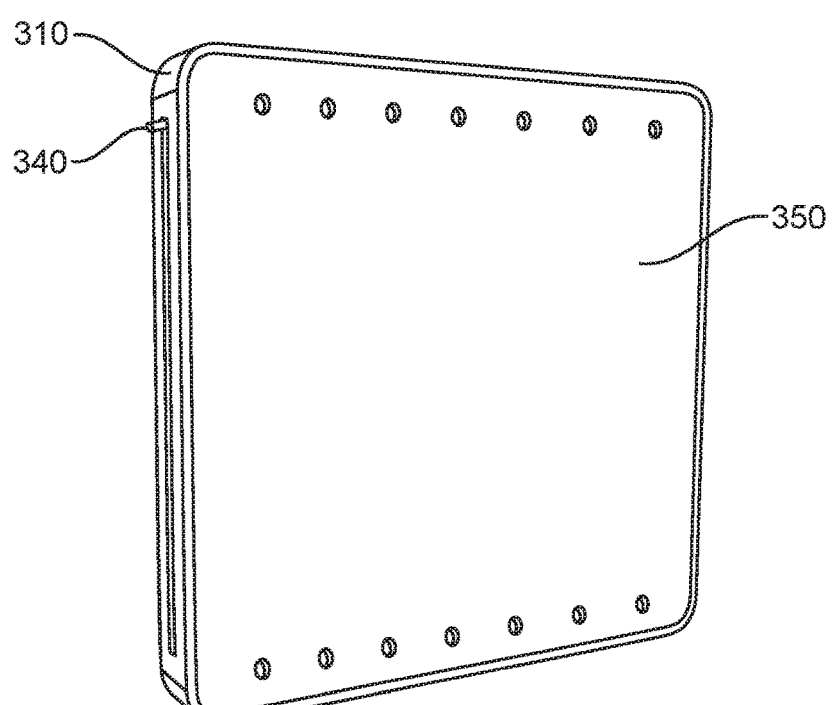
FIG. 5 is a rear perspective view of the apparatus of FIG. 4, according to an embodiment of the present invention.
Figure 6:
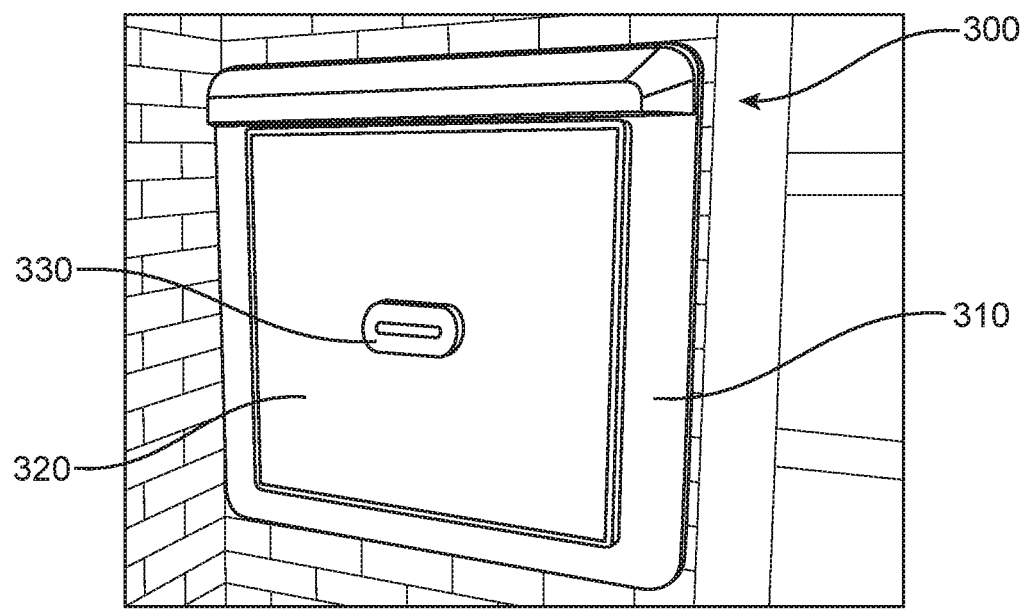
FIG. 6 shows the apparatus of FIG. 4 mounted to a wall, according to an embodiment of the present invention.

FIG. 4 shows a compact form of the apparatus, eBox retro advantage, which has only one enclosure and is more suitable for residential places, single offices, and rooms. The apparatus 300 comprises a frame 310 that can mount to a wall. As shown in FIG. 4, the apparatus is thin, while the size of the apparatus depends upon the desired size of the enclosure. The enclosure 320 is mounted to the frame 310. FIG. 4 shows the front side of the enclosure having a handle 330 at the outer surface of the front side. The handle 330 can be grabbed by hand to unfold the enclosure 320 from its nested configuration. Furthermore, it can be seen in FIG. 4 is a lever 340 protruding from a slot configured on the side of the frame 310. FIG. 5 shows the rear side of the frame 310. In one case, the rear side of the frame 310 can also be the rear side of the enclosure 320. FIG. 6 shows the apparatus 300 mounted on a wall.

Figure 7:
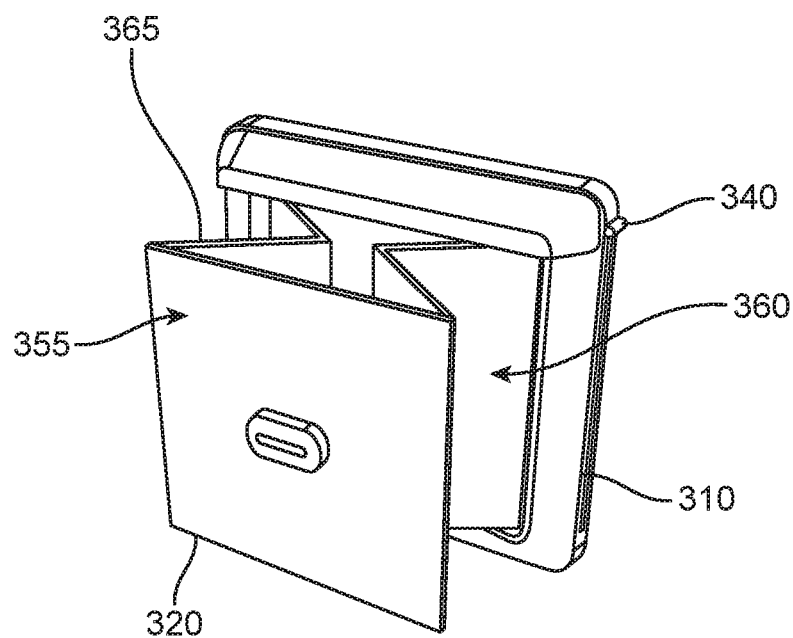
FIG. 7 shows the apparatus of FIG. 4 in a nested configuration, according to an embodiment of the present invention.
Figure 8:
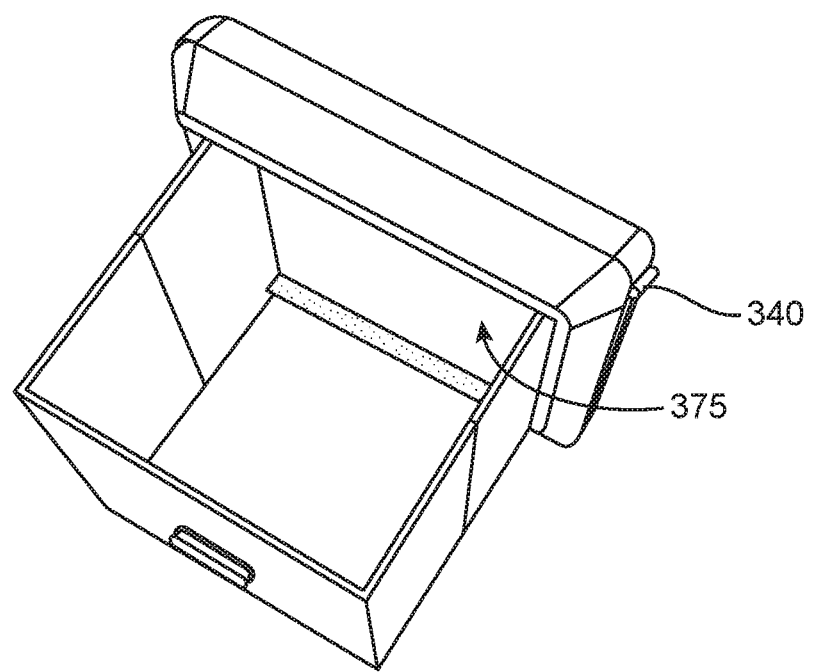
FIG. 8 shows the apparatus of FIG. 4 in an unfolded configuration, according to an embodiment of the present invention.
Figure 9:
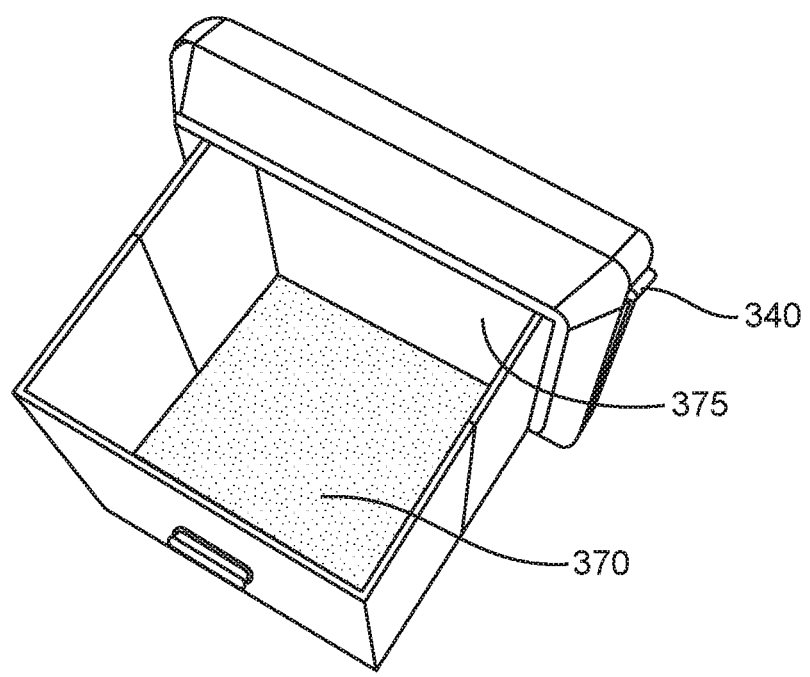
FIG. 9 shows the apparatus of FIG. 8 with the bottom side in extended configuration, according to an embodiment of the present invention.
Figure 10:
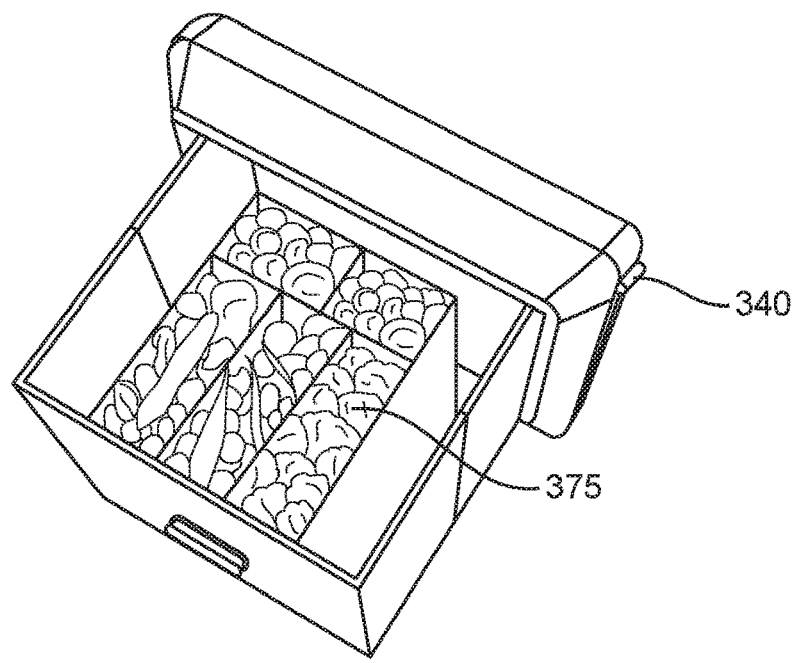
FIG. 10 shows the apparatus of FIG. 9 with deliveries, according to an embodiment of the present invention.

FIG. 7 shows the unfolding of the enclosure 320 from its nested configuration. The apparatus 300 in unused condition can be folded into a nested configuration, wherein the front side 355 of the enclosure collapses towards its rear side 375, thus saving space. To unfold the enclosure 320, the front side 355 of the enclosure 320 can be pulled outwards away from the frame 310. FIG. 7 shows the enclosure partially unfolded, showing the front side 355, a left side 360, and the right side 365. The left side 360 and the right side can be made of two panels joined by a hinge joint, such as the left side 360 and the right side can collapse inwards as shown in FIG. 7. FIG. 8 shows the enclosure 320 fully unfolded having the left side and the right side flat. FIG. 9 further shows the enclosure having a bottom side 370.

Figure 11:
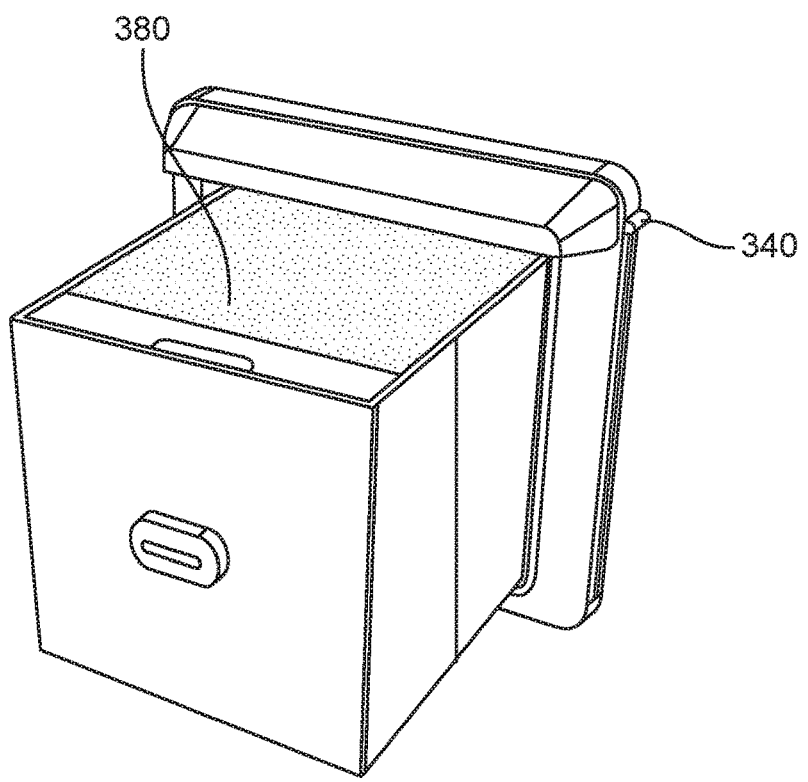
FIG. 11 shows the apparatus of FIG. 10 covered with a top cover, according to an embodiment of the present invention.

The apparatus 300 can include a first chamber and a second chamber each adjacent to the rear side 375. The width and area of the first chamber are commensurate with the width and area of the top side 380 (shown in FIG. 11), respectively. The width and area of the second chamber are commensurate with the width and area of the bottom side 370, respectively. The bottom side 370 is rigid enough to withstand the weight of the package contained in the enclosure upon the bottom side 370. Also, the bottom side 370 is flexible enough to be retracted into the second chamber. In one case, the bottom side automatically extends from the second compartment upon unfolding the enclosure. The bottom side can be provided with a spring mechanism that pulls the bottom side from the second chamber towards the front side. The full unfolding of the enclosure can trigger the spring mechanism. To return the bottom side into the second chamber, the rear end of the bottom side can be linked to a lever 340, shown in FIG. 4. The lever 340 can slide into the slot vertically, wherein the extending of the bottom side 370 from the second chamber causes the lever 340 to slide downwards. To retract the bottom side into the second chamber, the lever 340 can be pulled upwards resulting in pulling off the bottom side into the second chamber. In another case, the bottom side 370 can be manually extended from the second chamber and engaged to the front side for the storage of the package. It is to be noted that the disclosure describes a first compartment and a second compartment, however, the first compartment and the second compartment can be a single structure that can accommodate the top cover and the bottom side.

FIG. 9 shows a package placed into the enclosure 320. Once, the package has been placed in the enclosure, the top side or top cover 380 can be extended from the first chamber and engaged to the front side 350. The top cover in extending the position can be locked securing access to the inside of the enclosure. Once locked, the UV-lamps can be turned On by the control unit. Optionally, the refrigeration unit can also be started. To pick the package from the apparatus, the consumer can unlock the top cover using a remote control or the user device. Once, unlocked the top cover can be retracted into the first compartment gaining access to the interior of the enclosure. It is to be understood that the top cover is described to be manually withdrawn from the first chamber and manually pushed back, however, the top cover can also be motorized. Alternatively, the retracting of the top cover into the first chamber can be affected by a spring-loaded mechanism, which automatically pulls the top cover into the first chamber once the top cover is disengaged.

The consumer can then pick the package and close the apparatus. To close the apparatus, the bottom side can be retracted back into the second compartment. The lever alongside the frame can be pulled upwards by the consumer resulting in retracting of the bottom side into the second chamber. Once the bottom side is retracted, the front side of the enclosure can be pushed towards the rear side resulting in collapsing of the enclosure into its nested configuration. It is obvious that while pushing the front side, the left and right sides can be slightly pushed inwards, thereafter the whole enclosure folds into the nested configuration as shown in FIG. 4. The eBox retro advantage can be powered by a battery.

In one case, the apparatus according to the present invention may not only allow receiving the packages but also returning the packages. The package to be returned can be placed in the enclosure and the enclosure can be locked. The present invention can then inform the courier company to automatically pick up the apparatus. The courier company can be issued a temporary key that allows the apparatus to be opened for pick-up of the return package. Alternatively, the apparatus can be unlocked remotely using the user device when the courier person arrives for pick up. The apparatus according to the present invention can provide auto pick up notifications and drop-off alerts.

Figure 12:
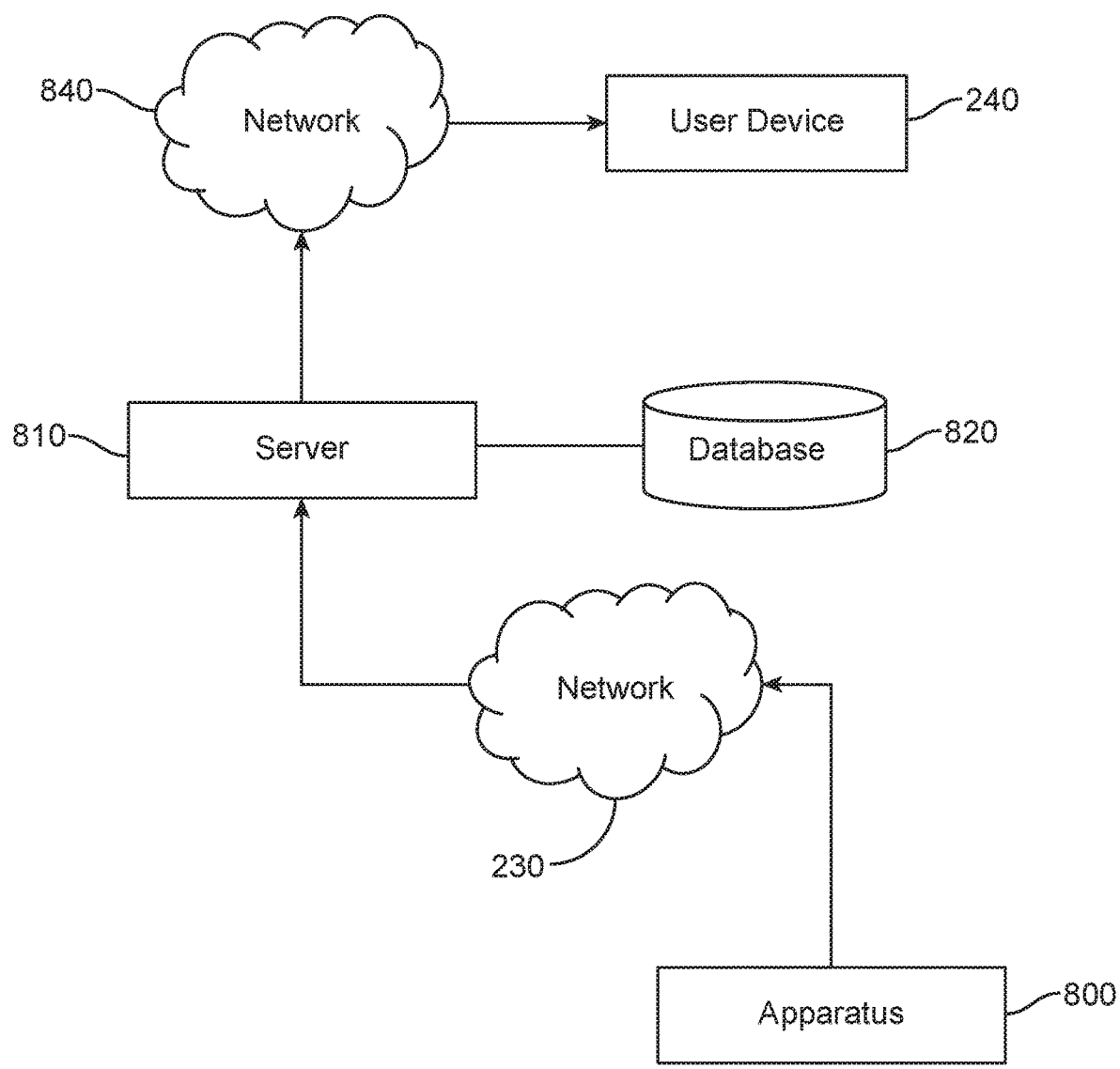
FIG. 12 shows an alternative embodiment of the present invention having a server connecting the apparatus to a user device.

FIG. 12 shows another exemplary embodiment of the present invention in which the apparatus 800 according to the present invention can be connected to a server 810 through the network 230. The server 810 is further connected to a database 820. The user device 240 can be remotely connected to the server 810 through the network 840. The network 840 and the network 230 can be same or different networks. In one case, the server 810 can host the electronic wallets, subscriptions, generating and issuing electronic keys, members profiles and account details, GPS coordinates of the apparatus, and like. The server 810 may allow communicating with the courier company for deliveries and pick-ups of return. The server 810 can provide GPS coordinates of the consumer address to the courier company. Moreover, the servers allow generating and sharing electronic keys for locking and unlocking the apparatus 800. The data related to above including customers account details can be stored in the databases. In one case, the server 810 and the database 820 can be embodied in cloud servers. The user device 240 can be provided with an application, the application can be made for android, iOS and like operating systems.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. An apparatus for receiving and securing a package, the apparatus comprising:
   a frame mounted to a stand;
   a plurality of enclosures encased into the frame, each of the plurality of enclosures having an opening for gaining access into interior of the each of plurality of enclosure, each of the plurality of enclosures comprises:
      a door switchable between an open position and a closed position, in the closed position the door closes the opening, in the open position the interior is accessible,
      a digital lock coupled to the door for securing switching of the door, and
      at least one ultraviolet (UV)-lamp positioned inside the enclosure and configured to produce UV radiation in a UV-C range;
   a control unit, wherein the digital lock and the UV-lamp are coupled to the control unit;
   a refrigeration unit configured for regulating temperature inside at least one of the plurality of enclosures within a predetermined range; and
   at least one radio-frequency identification (RFID) reader coupled to the control unit, the at least one RFID reader configured to read the predetermined range of temperature from a tag coupled to a package, the package stored in the at least one of the plurality of enclosures,
   wherein the control unit, upon receiving the predetermined range of temperature, configures the refrigeration unit with the predetermined range of temperature.

2. The apparatus of claim 1, further comprising a camera and a microphone coupled to the frame.

3. The apparatus of claim 1, wherein the stand is mounted to the ground, and the door of each of the plurality of enclosures having a unique address.

4. The apparatus of claim 1, wherein the control unit further comprises a network circuitry configured for connecting to a wireless network.

5. The apparatus of claim 4, wherein the wireless network is a cellular network or a Wi-Fi network.

6. The apparatus of claim 4, wherein the control unit is wirelessly coupled to a user device through the wireless network, the user device is configured to send instructions to the control unit, and the control unit is configured to send notifications to the user device.

7. The apparatus of claim 6, wherein the user device is a smartphone.

8. The apparatus of claim 6, wherein the control unit is further configured for:
   receiving an instruction to turning the at least one UV-lamp ON and Off; and
   upon receiving the instruction, setting a timer for the at least one UV-lamp.

9. The apparatus of claim 1, wherein the control unit further comprises a timing circuit configured for setting a duration of the at least one UV-lamp.

10. The apparatus of claim 1, wherein the apparatus further comprises a remote control, and the control unit is operably coupled to the remote control.

11. An apparatus for receiving and securing a package, the apparatus comprising:
   a frame that can be mounted to a wall;
   an enclosure, wherein
      the enclosure is encased into the frame,
      the enclosure having an opening for gaining access to an interior of the enclosure,
      the enclosure having a rear side, a front side, a left side, a right side, a bottom side, and a top cover, the top cover is configured to switch between a retracted position and an extended position, in the extended position the top cover closes the opening of the enclosure, in the retracted position the interior of the enclosure is accessible, each of the left side and the right side is made of two panels joined by a hinge joint, such that the left side and the right side can collapse inwards, and the bottom side is configured to switch between a retracted position and an extended position;

a control unit;

a digital lock coupled to the top cover for securing switching of the top cover, the digital lock operably coupled to the control unit; and at least one ultraviolet (UV)-lamp positioned inside the enclosure and configured to produce UV radiation in a UV-C range, the at least one UV-lamp operably coupled to the control unit.

12. The apparatus of claim 11, wherein:
the apparatus further comprises:
a first chamber and a second chamber adjacent the rear side of the enclosure, and
a width and an area of each of the first chamber and the second chamber are commensurate with a width and an area of each of the top cover and the bottom side respectfully,
the top cover is configured to retract into the first chamber, and
the bottom side is configured to retract into the second chamber.

13. The apparatus of claim 12, wherein:
the bottom side is configured with a spring mechanism to extend the bottom side from the second chamber,
a rear end of the bottom side is coupled to a lever, the lever protrudes from a vertical slot configured in the frame,
the lever is configured to be grabbed by hand for sliding the lever along with the vertical slot, and
pulling the lever upwards along the vertical slot retracts the bottom side into the second chamber.

14. The apparatus of claim 4, wherein the control unit is configured to:
receive an instruction, from a remote device, through the wireless network; and
upon receiving the instruction, unlock the digital lock.

15. A method for receiving and securing a package, the method comprising:
providing an apparatus, the apparatus comprises:
a frame,
a plurality of enclosures encased into the frame, each of the plurality of enclosures having an opening for gaining access into an interior of each of the plurality of enclosures, each of the plurality of enclosures comprises:
a door switchable between an open position and a closed position, in the closed position the door closes the opening, in the open position the interior is accessible,
a digital lock coupled to the door for securing switching of the door, and
at least one ultraviolet (UV)-lamp positioned inside the enclosure and configured to produce UV radiation in a UV-C range,
a control unit, wherein the digital lock and the UV-lamp are coupled to the control unit,
a refrigeration unit configured for regulating temperature inside at least one of the plurality of enclosures within a predetermined range, and
at least one RFID reader coupled to the control unit, the at least one RFID reader configured to read the predetermined range of temperature from a tag coupled to a package;
opening the door of the at least one of the plurality of enclosures;
receiving the package in the at least one of the plurality of enclosures;
closing the door of the at least one of the plurality of enclosures, wherein upon closing, the door of the at least one of the plurality of enclosures is locked;
reading, by the control unit of the at least one of the plurality of enclosures, the predetermined range of temperature from the tag; and
configuring, by the control unit, temperature of the refrigeration unit of the at least one of the plurality of enclosures to the predetermined range of temperature.

16. The method of claim 15, further comprising:
receiving, by the control unit of the at least one of the plurality of enclosures, from a remote device, through a wireless network, an instruction to unlock the door of the at least one of the plurality of enclosures, wherein the at least one of the plurality of enclosures has a unique address that is associated with the remote device.

17. The method of claim 15, further comprising:
receiving, by the control unit of the at least one of the plurality of enclosures, from a remote device, through a wireless network, an instruction to turn ON the at least one UV-lamp positioned in the at least one of the plurality of enclosures.

\* \* \* \* \*